United States Patent [19]

Ikuta et al.

[11] 4,135,980

[45] Jan. 23, 1979

[54] CHOLINE OXIDASE

[75] Inventors: Shigeru Ikuta; Yoshifumi Horiuchi; Hideo Misaki; Kazuo Matsuura; Shigeyuki Imamura; Naoki Muto, all of Shizuoka, Japan

[73] Assignee: Toyo Jozo Kabushiki Kaisha, Shizuoka, Japan

[21] Appl. No.: 789,990

[22] Filed: Apr. 22, 1977

[30] Foreign Application Priority Data

Apr. 26, 1976 [JP] Japan .................................. 51-47992

[51] Int. Cl.$^2$ ...................... C12D 13/10; G01N 31/14
[52] U.S. Cl. .................................. 195/62; 195/66 R; 195/103.5 R
[58] Field of Search ........... 195/62, 65, 66 R, 103.5 R

[56] References Cited
PUBLICATIONS

Methods in Enzymology I, 674–678 (1955).
Method in Enzymology V, 562–570 (1962).

*Primary Examiner*—Lionel M. Shapiro
*Attorney, Agent, or Firm*—Young & Thompson

[57] ABSTRACT

A novel enzyme choline oxidase is produced by culturing a microorganism belonging to the genus Arthrobacter, and particularly the species *Arthrobacter globiformis* B-0577 FERM-P No. 3518, NRRL B-11097, and isolating the choline oxidase thus produced from the culture medium. Choline oxidase is useful for the determination of choline or betaine aldehyde in a sample by mixing the new product with the sample and then measuring the generated hydrogen peroxide, betaine or consumed oxygen.

21 Claims, 13 Drawing Figures

CHOLINE OXIDASE

This invention relates to a novel enzyme choline oxidase, a manufacturing process therefor, and an analytical method using choline oxidase.

Choline dehydrogenase [EC. 1.1.99.1. choline: (acceptor) oxidoreductase] and betaine aldehyde dehydrogenase [EC. 1.2.1.8. betaine aldehyde:NAD oxidoreductase] are hitherto known enzymes which act on choline or choline aldehyde as a substrate. These enzymes however require the coenzyme in their enzyme actions and utilize molecular oxygen as a terminal electron to produce $H_2O$ [Methods in Enzymology, V, 562–570 (1962), ibid. I, 674–678 (1955), Academic Press] and hence these are classified as dehydrogenase. The betaine aldehyde dehydrogenase was isolated from a strain of *Pseudomonas aeruginosa* A-16 and purified and was found to have a molecular weight of about 145,000 (by gel filtration), isoelectric point: 5.1, optimum pH: 8.0–9.0 and stable pH about ph 7.5.

We have found that an enzyme, which catalyzes an oxidation reaction from choline to betaine, was produced in bacterial strain B-0577 belonging to genus Arthrobacter isolated from a soil sample collected in Kagoshima, Japan, and have isolated a purified enzyme.

This enzyme has the physico-chemical properties of isoelectric point 4.6 (electrophoresis by carrier type ampholyte) and molecular weight about 84,000 ± 2,100 (gel filtration by Sephadex G-150), has substrate specificites for choline and betaine aldehyde, requires no coenzyme, and the substrates react directly with oxygen in the enzyme action.

This novel enzyme choline oxidase catalyzes the reaction wherein one mole of choline is oxidized to betaine through betaine aldehyde to form two moles of hydrogen peroxide, or one mole of betaine aldehyde is oxidized to betaine to form one mole of hydrogen peroxide.

The strain B-0577 has taxonomic properties as follows:

A. Macroscopic observation on various media, cultured at 26° C. for 18–42 hours.
(1) Bouillon agar plate:
  Growth: abundant, circular, entire, convex.
  Color of colony: grayish white (hue 1½ ca) to pale yellow (hue 1½ ga), no diffusible pigment.
(2) Bouillon agar slant:
  Growth: abundant, filiform growth, opalescent.
  Color of colony: grayish white (hue 1½ ca) to pale yellow (hue 1½ ga), no diffusible pigment.
(3) Bouillon broth:
  No or very thin pellicle formation on surface growth.
  Cultured broth; turbid and slight sediment, non-transparent.
(4) Bouillon gelatin stab:
  Growth: good, grown on surface, no gelatin liquefaction.
(5) Litmus milk:
  Growth: weak, peptonization at about two weeks, sometimes soft coagulation or alkalization, no litmus reduction.
  Color designations were taken from "Color Harmony Manual" (Container Corporation of America, 1958 4th Ed.)

B. Microscopic observation:
(1) Shape and size of cells on bouillon agar plate (six hours cultivation): rod, 0.5–0.8 × 1.5–2.0μ. (18 hours cultivation): spherule, 0.5–0.8μ.
(2) Polymorphism: in bouillon broth culture, sometimes form T-shaped or Y-shaped cells.
(3) Motility: none (on soft agar).
(4) Spore: none.
(5) Gram's stain: young cells: positive; old cells: negative.
(6) Acid-fast stain: negative.

C. Physiological properties:
Nitrate reduction: negative.
Denitrification reaction: negative.
MR test: negative.
VP test: negative.
Indole formation: negative.
Hydrogen sulfate formation: weakly positive.
Starch hydrolysis: weakly positive.
Citrate utilization, Koser medium: negative. Christensen medium: positive.
Nitrate utilization: negative.
Ammonium utilization: negative.
Pigment formation: negative.
Urease: positive.
Oxidase: weakly positive.
Catalase: positive.
Growth pH: pH 4.0–11.0
Growth temperature: 5°–37° C.
Behavior in oxygen: aerobic.
Cellulose hydrolysis: negative.
Casein hydrolysis: negative.
O-F test*: O (oxidative decomposition).
Acid formation from sugar (no gas formation)**:
  within one week: glucose, inositole.
  within two weeks: cellobiose, erythritol, fructose, maltose, mannitol, mannose, sorbitol, sucrose, trehalose, starch.
  no acid formation: L-arabinose, dulcitol, esculin, galactose, glycerin, lactose, melezitose, melibiose, salicin, sorbose, xylose.

* O-F test medium: modified medium; $NH_4H_2PO_4$ 1 g, yeast extract powder 1 g, KCl 0.2 g, $MgSO_4.7H_2O$ 0.2 g, glucose 10 g, agar powder 2g, Bromthymol Blue 0.02 g, distilled water 1 lit., pH 7.2.
** basal medium: $NH_4H_2PO_4$ 1 g, yeast extract powder 1 g, KCl 0.2 g, $MgSO_4.7H_2O$ 0.2 g, agar powder 2 g, Bromthymol Blue 0.02 g, distilled water 1 lit., ph 7.2.

Consulting Bergey's Manual of Determinative Bacteriology, 8th Ed. 1974, the strain B-0577 having the taxonomical properties hereinabove, especially Gram positive, non-acid-fast and non-motile bacillus or coccus, and branched but not filamentous, oxidative decomposition of sugar, catalase positive, weakly positive oxidase and non-decomposition of cellulose, is referred to as belonging to genus Arthrobacter in Coryneform group bacteria.

Comparison of the strain B-0577 with the type cultures of seven species belonging to genus Arthrobacter described in the above Bergey's Manual, 1974, is as follows:

In Table:
  + = positive reaction, or acid formation from sugar within one week.
  (+) = weakly positive reaction, or acid formation within 1–2 weeks.
  − = negative reaction.

TABLE

| microorganism item | strain B-0577 | Arthrobacter simplex IFO 12069 | Arthrobacter globiformis IFO 12137 | Arthrobacter citreous IFO 12957 | Arthrobacter tumescens IFO 12960 | Arthrobacter terregens IFO 12961 | Arthrobacter duodecadis IFO 12959 | Arthrobacter flavescens | Remarks |
|---|---|---|---|---|---|---|---|---|---|
| Culturing temperature: 26° C. | | | | | | | | | |
| Gram's stain | + | + | + | + | + | + | + | + | |
| acid-fast stain | − | − | − | − | − | − | − | − | |
| shape | S-R | S-R | S-R | S-R | S-R | S-R | S-R | S-R | |
| spore | − | − | − | − | − | − | − | − | |
| oxidase | (+) | − | + | + | − | + | | | |
| catalase | + | + | + | + | + | + | | | |
| urease | − | − | − | − | − | − | | | SSR medium |
| urease | + | − | + | − | − | − | | | Christensen's medium 2 days culture |
| gelatin liquefaction | − | − | − | − | − | − | | + | Frazier method 2 days culture |
| starch hydrolysis | (+) | + | − | (+) | − | (+) | − | + | iodometry (Gram's iodine) |
| casein hydrolysis | − | − | − | − | − | + | | | |
| cellulose hydrolysis | − | − | − | − | − | − | − | − | |
| indole formation | − | − | − | − | − | − | | | |
| $H_2S$ formation | (+) | + | (+) | − | + | − | | | lead acetate paper method |
| VP test | − | − | − | − | − | − | | | |
| MR test | − | − | − | − | − | − | | | |
| nitrate reduction | − | − | − | + | + | + | + | + | |
| litmus milk | peptonization | peptonization | weak peptonization | weak peptonization | coagulation | no change | | | |
| citrate utilization | − | − | − | − | − | − | | | simmons' medium |
| citrate utilization | + | + | + | + | + | − | | | Christensen's medium |
| O-F test | 0 | 0 | 0 | 0 | 0 | NT | | | |
| color of Colony | pale yellow | grayish white | grayish white | yellow | grayish white | yellow | | | |
| Arabinose | − | − | + | + | (+) | − | | | |
| cellobiose | (+) | − | (+) | − | (+) | − | | | |
| dulcitol | − | − | + | − | − | − | | | |
| erythritol | (+) | − | − | − | − | − | | | |
| esculin | − | − | − | − | − | − | | | |
| fructose | (+) | (+) | + | (+) | (+) | − | | | |
| galactose | − | − | (+) | − | (+) | − | | | |
| glucose | + | + | + | (+) | (+) | − | | | |
| glycerin | − | + | + | − | − | − | | | |
| inositol | + | − | (+) | − | (+) | − | | | |
| lactose | − | − | − | − | (+) | − | | | |
| maltose | (+) | − | (+) | − | − | − | | | |
| mannitol | (+) | − | + | − | − | − | | | |
| mannose | (+) | − | + | + | (+) | − | | | |
| melezitose | − | − | + | − | − | − | | | |
| melibiose | − | − | + | − | (+) | − | | | |
| raffinose | − | − | + | − | ((+)) | − | | | |
| salicin | − | − | + | + | − | − | | | |
| sorbose | − | − | − | − | − | − | | | |
| sorbitol | (+) | − | + | (+) | ((+)) | − | | | |
| starch | (+) | − | + | − | − | − | | | |
| sucrose | (+) | (+) | + | (+) | ((+)) | − | | | |
| trehalose | (+) | (+) | (+) | (+) | − | − | | | |
| xylose | − | − | + | + | +− | − | | | |

*Arthrobacter duodecadis* IFO 12959 and *Arth. flavescens* were only referred from the description in Bergey's Manual, 1974, and the former did not grow on nutrient agar medium.

As a result, the taxonomical properties of the strain B-0577 were identical with those of *Arthrobacter globiformis* IFO 12137, except the color the colony, starch decomposition (slightly different) and acid formation from some sugars. As for the color of the colony, *Arthrobacter globiformis* does not produce characteristic pigment on nutrient agar; however in some strains water-immiscible lemon yellow pigment is produced. Further both strains produce acid from starch (starch decomposition), furthermore *Arthrobacter globiformis* IFO 12137 produces acid from all of the sugars, wherefrom the strain B-0577 produces acid, except erythritol. Thereby the strain B-0577 is referred to as *Arthrobacter globiformis* and designated as *Arthrobacter globiformis* B-0577. This strain was deposited for permanent collection in the Institute for Microbial Industry and Technology, Agency of Industrial Science and Technology, Japan, as deposition No. FERM-P No. 3518. The strain was also deposited in ARS, U.S.A. as NRRL No. NRRL B-11097.

Since the novel enzyme choline oxidase is an enzyme wherein choline and betaine aldehyde are substrates thereof, choline or betaine aldehyde in a liquid sample can be quantitatively determined by treating the said sample with choline oxidase, thereby measuring the thus-generated hydrogen peroxide, betaine or consumed oxygen.

An object of the present invention is to provide a novel enzyme choline oxidase having at least the following properties:

Substrate specificity: for a compound of the formula wherein $R_1$ is —$CH_2OH$ or —CHO.

Optimum pH: pH 8 (tris-HCl buffer)

Isoelectric point: 4.6 (electrophoresis on carrier type ampholyte)

Molecular weight: 84,000 ± 2,100 [gel filtration using Sephadex G-150 (trade name)]

Enzyme action: catalyzes reaction [I] and/or [II]:

Another object of the present invention is to provide a process for the production of a novel enzyme choline oxidase which comprises culturing choline oxidase-producing microorganisms belonging to genus Arthrobacter in a nutrient culture medium and isolating the choline oxidase from the cultured mass.

A further object of the present invention is to provide a method for the quantitative determination of choline or betaine aldehyde.

A still further object of the present invention is to provide an analytical method for liquid samples containing choline or betaine aldehyde which comprises treating a said sample with choline oxidase, and measuring the thus-generated hydrogen peroxide, betaine or consumed oxygen.

Still another object of the present invention is to provide a clinical diagnostic method and reagent for assaying choline, betaine aldehyde, choline derivatives or betaine aldehyde derivatives in body fluids.

Other objects, features and advantages of the present invention will become apparent from a consideration of the following description, taken in connection with the accompanying drawings, which are graphs or diagrams illustrating the present invention, and in which more particularly:

In an embodiment of the present invention, *Arthrobacter globiformis* B-0577 FERM-P No. 3518 is cultured in a conventional medium for antibiotic or enzyme production. Submerged aeration culture is preferable for industrial production.

A conventional medium for microorganisms can preferably be used. As for the nitrogen sources, assimilable nitrogen sources such as corn steep liquor, soybean powder, peptone, meat extracts, yeast extracts, ammonium sulfate, ammonium chloride, or the like can be used. Assimilable carbon sources such as molasses, glucose, starch hydrolyzates or the like can preferably be used. Various inorganic salts such as sodium chloride, potassium chloride, magnesium sulfate, potassium hydrogen phosphate or potassium dihydrogen phosphate, and antifoaming agents are optionally used. The addition of choline to the medium stimulates the production of choline oxidase. Ten times higher productivity can be achieved by the addition of 0.5–1% of choline.

The culturing temperature can be changed within the ranges for growth of microbial cells and production of an enzyme, and is preferably 25°–30° C. The culturing time can be altered depending on conditions and is usually 15–50 hours. Culturing should naturally be terminated when the choline oxidase production is substantially complete.

Choline oxidase is an endo-enzyme which exists in the cells of microorganisms.

Embodiments of the extraction of choline oxidase from the cultured mass are as follows. The cultured mass is filtered and the wet cells are suspended in a buffer such as tris-HCl buffer, and disrupted by treatment with lysozyme, sonication or French press. Lysozyme treatment is preferable for high yield and specific activity of the enzyme. The thus-obtained crude choline oxidase is purified by conventional isolation and purification methods for protein and enzyme. For example, fractional precipitation with acetone or isopropanol and salting out with ammonium sulfate are preferably applied. Further purification can be achieved by for example, electrophoresis or chromatography in which the crude choline oxidase is dissolved in tris-HCl buffer and chromatographed using ion exchangers such as cross-linked diethylamino ethyl-cellulose or -dextran gel, and gel filtration agents such as dextran gel or polyacrylamide gel. Purified choline oxidase can be stored as a lyophilized powder.

Choline oxidase of the present invention has the following physico-chemical properties:

(1) Enzyme action:
Choline is oxidized to form betaine aldehyde and betaine aldehyde is oxidized to betaine.

Oxidation of one mole of choline liberates one mole of betaine aldehyde and one mole of hydrogen peroxide, and further the one mole of betaine aldehyde is oxidized to generate one mole of betaine and one mole of hydrogen peroxide. Ultimately one mole of choline generates one mole of betaine and two moles of hydrogen peroxide. And one mole of betaine aldehyde generates one mole of betaine and one mole of hydrogen peroxide.

(2) Enzyme assay:
To a reaction mixture (0.50 ml) consisting of 0.2 mole tris-HCl buffer (pH 8.0, 0.05 ml), 4-aminoantipyrine (3 mg/ml, 0.05 ml), 0.1% phenol (0.10 ml), peroxidase (2 $\mu$/mg, 0.10 ml), 0.1 mole choline chloride (0.10 ml) and distilled water (0.10 ml) is added the enzyme solution (5 $\mu$l) and incubated at 37° C. for 5 minutes. Ethanol (2.5 ml) is added to cease the reaction.

A unit of enzyme activity is defined as the activity of enzyme which generates 1 $\mu$mole of hydrogen peroxide per minute. The activity of the enzyme (units/ml) is given by:

Units/ml = $\Delta A_{480}$/min × 14 where $\Delta A_{480}$ is the change per minute in absorbance at 480 nm.

(3) Substrate specificity:
Relative activity on several substrates is as follows:

| Substrate | Relative activity |
|---|---|
| Choline | 100.0 |
| Betaine aldehyde | 50.0 |
| N-methylamino ethanol | 3.6 |
| N,N-dimethyl aminoethanol | 5.2 |
| Monoethanolamine | 0.4 |
| Diethanolamine | 0.0 |
| Triethanolamine | 3.6 |

The enzyme has the highest activity on choline and betaine aldehyde.

Figure 1:
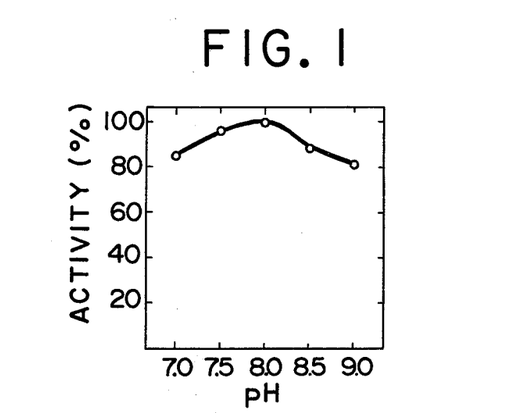
FIG. 1: optimum pH of choline oxidase.

(4) Optimum pH:
pH as shown in FIG. 1. Choline s used as substrate.

Figure 2:
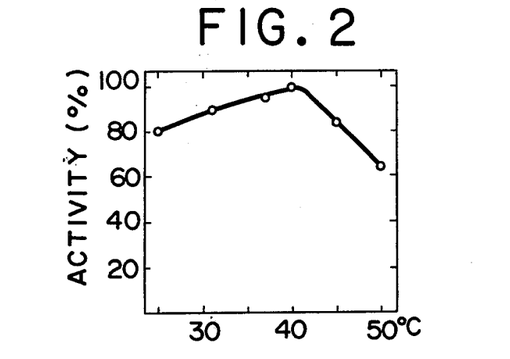
FIG. 2: optimum temperature of choline oxidase.

(5) Optimum temperature:
Around 40° C. as shown in FIG. 2. Substrate: choline.

Figure 3:
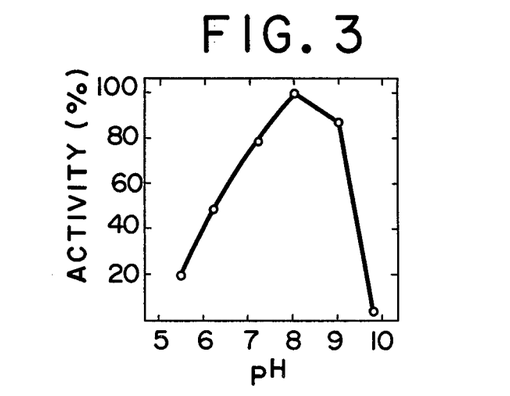
FIG. 3: pH-stability of choline oxidase.

(6) pH stability:
Dimethylglutarate buffer for pH 6-7, tris-HCl buffer for pH 7-8 and glycine-NaOH buffer for pH 9-10 are used. To the 25 m mole of each buffer, 0.1 ml enzyme solution (protein 10 $\mu$g/ml, 5 $\mu$l) was added and allowed to stand for 30 minutes at 37° C. After pH is adjusted by adding 0.5 mole tris-HCl buffer (pH 8.0, 0.05 ml) thereto, enzyme activity is determined. Choline is used as the substrate and as shown in FIG. 3, the stable pH is about pH 8.

Figure 4:
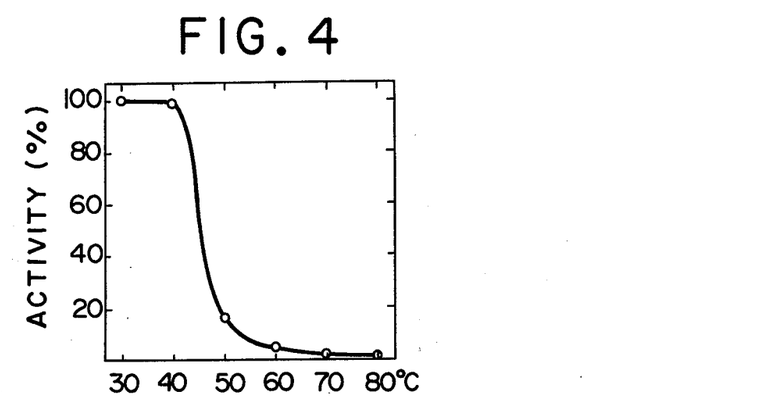
FIG. 4: heat stability of choline oxidase.
Figure 5:
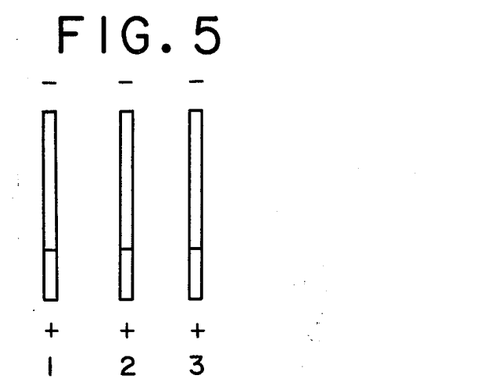
FIG. 5: electrophoretic pattern of choline oxidase.

(7) Heat stability:
Heat stability of the enzyme is determined by incubating 10 m mole tris-HCl buffer (1 ml, pH 8.0) containing enzyme (protein 10 $\mu$g/ml) at various temperatures for 10 minutes using choline as a substrate. As shown in FIG. 4 the enzyme is stable below about 40° C. and the activity is rapidly decreased above 40° C.

(8) Effect of several substances:
Effect of several substances on the enzyme activity is examined by adding 5 m moles of metal ions or 0.1% w/v of detergent.

| Substance added | Relative activity |
|---|---|
| $CaCl_2$ | 101.0 |
| $MgCl_2$ | 100.0 |
| $FeCl_3$ | 0.0 |
| $ZnCl_2$ | 7.9 |
| $MnCl_2$ | 97.7 |
| $CoCl_2$ | 30.7 |
| $MoCl_2$ | 58.0 |
| KCl | 93.2 |
| NaCl | 96.6 |
| $NH_4Cl$ | 100.0 |
| LiCl | 96.6 |
| $BaCl_2$ | 103.4 |
| Triton X-100 (trade name) | 95.5 |
| Adekatol SO-120 | 105.7 |
| Sodium lauryl sulfate | 94.3 |
| Sodium deoxycholate | 94.3 |
| Tween 20 | 96.6 |
| Sodium lauryl benzenesulfonate | 91.0 |
| Cation DT 205 | 65.9 |
| No addition | 100.0 |

(9) Molecular weight:
84,000 ± 2,100 [Sephadex G-150 gel filtration]

(10) Isoelectric point: 4.6 (electrophoresis using carrier type anpholyte)

(11) Electrophoresis:
The homogeneity of the purified enzyme preparation was checked by polyacrylamide disc gel electrophoresis. The electrophoresis was carried out in 50 mM tris-glycine buffer (pH 8.3) at a constant current of 2 mA per column (5 × 80 mm) for 150 minutes at 15° C., as described by Davis (Ann. N.Y. Acad. Sci., 121, 404–427).

For detection of the protein band, the gel was fixed and stained with Amide Black 10B in 7% acetic acid. A single deep blue band is observed as shown in FIG. 5-1.

Further, the band of the enzyme is detected by placing the gel containing the electrophoresed sample in the following reaction mixture at 37° C. for 20–30 minutes.

Reaction mixture: (total 10 ml)
0.2 M tris-HCl buffer: 1.0 ml
chromogen solution*: 2.0 ml
0.1 M substrate solution**: 1.0 ml
distilled water: 6.0 ml

* chromogen solution, comprising 0.1 mole tris-HCl buffer (10 ml), 5 mg/ml o-dianisidine ethanol solution (0.3 ml) and peroxidase (10 units).
** aqueous solution of choline chloride or betaine aldehyde.

Single red band as shown in FIG. 5-2 is observed by using choline chloride as substrate and single red band is also observed as shown in FIG. 5-3 when the betaine aldehyde is used as substrate. The stained gels are fixed by 7% acetic acid after washing with water.

As observed in FIGS. 5-1, 2, 3, electrophoretic mobilities on the gel are identical and shown as a single band, whereby the purified choline oxidase is identified as a single protein.

(12) Identification and determination of reaction products of choline oxidase-catalyzed oxidation:
A mixture (0.5 ml) containing choline or betaine aldehyde (0.01–0.05 $\mu$mole), tris-HCl buffer (pH 8.0, 10 $\mu$mole), 4-aminoantipyrine (150 $\mu$g), phenol (100 $\mu$g), peroxidase (0.2 unit) and choline oxidase (0.25 unit) is incubated at 37° C. for 25 minutes and absorbance at 480 nm is measured after adding ethanol (2.5 ml).

A standard curve is prepared by adding aliquot portions of hydrogen peroxide in place of choline or betaine aldehyde.

Figure 6:
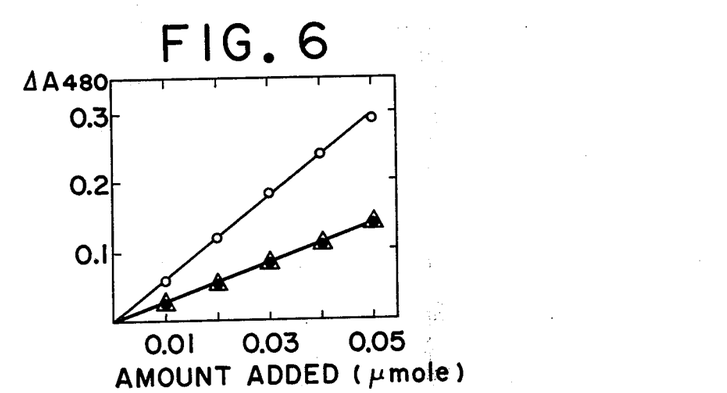
FIG. 6: standard curves of choline, betaine aldehyde and hydrogen peroxide.

The result is shown in FIG. 6 in which o—o indicates the result using choline as substrate, •—• is a result using betaine aldehyde as substrate and Δ—Δ indicates the result using hydrogen peroxide instead of a substrate. FIG. 6 indicates that the enzyme catalyzes the reactions wherein one mole of choline generates two moles of hydrogen peroxide and one mole of hydrogen peroxide is generated from one mole of betaine aldehyde.

Oxygen consumption determined by an oxygen electrode proves that two moles of oxygen are consumed during the oxidation of one mole of choline and one mole of oxygen is consumed during the oxidation of one mole of betaine aldehyde.

Betaine is quantitatively determined by adjusting the pH of the reaction mixture to 1, concentrating the mixture up to 100 times after activated carbon treatment and assayed by the Reinecke salt method. One mole of betaine is formed from one mole of choline or one mole of betaine aldehyde.

As hereinabove explained, the choline oxidase of the present invention does not require a coenzyme for the oxidation of choline and betaine aldehyde, and the substrate directly reacts with oxygen to generate hydrogen peroxide and the enzyme has different physico-chemical properties, whereby the choline oxidase is confirmed as the novel enzyme as compared with prior known choline dehydrogenase and betaine aldehyde dehydrogenase.

The novel choline oxidase can be used for the analysis of liquid samples containing choline or betaine aldehyde. Further, choline oxidase can be used for assaying the purity of choline and betaine aldehyde, a quantitative determination of derivatives of choline and betaine aldehyde, and an assay of the activity of enzymes which act on the derivatives of choline or betaine aldehyde to form choline or betaine aldehyde.

A sample containing choline or betaine aldehyde is, for example, an aqueous solution or medium of choline or betaine aldehyde, or an aqueous solution containing choline or betaine aldehyde liberated from the derivatives thereof. More particular examples are blood, serum, body fluid, tissue homogenate and the like. Therefore, choline oxidase can be used for clinical diagnosis directly or in combination with other chemical or enzymatic systems.

Examples of choline derivatives are physiological phospholipids such as lysolecithin, lecithin and sphingomyelins, biological substances such as acetylcholine, cytidyl phosphate choline and phosphorylcholine, or synthetic compounds such as benzoylcholine, propionylcholine, butylylcholine and succinylcholine. These substances are the derivatives of choline which can liberate choline by chemical or enzymatic means. Examples of liberation of choline from its derivatives are for example chemical methods such as alkaline or acid hydrolysis, and enzymatic methods such as with phospholipase C obtained from *Clostridium welchii* or *Bacillus cereus* and alkaline phosphatase obtained from bovine, porcine or chicken small intestinal mucosa, bovine liver or *E. coli;* phospholipase D obtained from cabbage, *Streptomyces hachijoensis* A 1143 or *Streptomyces chromofuscus* A-0848; and choline esterase obtained from bovine blood cells, electric eel, horse serum or human serum. The above-mentioned enzymes and origins thereof are only illustrative and are not to be construed as limiting; therefore, the enzymes having phospholipase C, alkaline phosphatase, phospholipase D or choline esterase activity can be used. The reaction on lecithin with phospholipase C and alkaline phosphatase can be illustrated in that lecithin is hydrolyzed to diglyceride and phosphorylcholine by phospholipase C and the liberated phosphorylcholine is split to inorganic phosphate and choline by the action of alkaline phosphatase. Phospholipase D hydrolyzes lecithin to phosphatidic acid and choline. Benzoylcholine is hydrolyzed to benzoic acid and choline by choline esterase. These enzymatic methods are given only as examples and any means, which generate choline or betaine aldehyde from the derivatives thereof, can advantageously be used. The enzymatic pre-treatment of the derivatives of choline and betaine aldehyde can be done separately to liberate choline and betaine aldehyde, or if the enzymatic pretreatment is very short or simple, it can be performed simultaneously with the addition of choline oxidase. Choline oxidase can be used as a buffer solution or in microcapsulated form or immobilized form. The amount of choline oxidase to be added is greater than one unit and preferably 1.5 to 5 units and the purity required is as high as possible; but it is not always necessary to use the highest purity grade.

In the incubated mixture of the sample and choline oxidase, hydrogen peroxide and betaine are liberated therein and a corresponding amount of oxygen is consumed therefrom. The determination of oxygen is preferably performed by the oxygen electrode method. Betaine can preferably be determined by the Reineckate method or the gas chromatographic method of esterified betaine. Hydrogen peroxide can advantageously be determined by the colorimetric method using reaction systems with one or more coloring reagents. Preferable colorimetric methods are, for example, the reaction of hydrogen peroxide with a quaternary titanium compound and xylenol orange, or with phenol, 4-aminoantipyrine and peroxidase. In the latter reaction, the presence of phenol inhibits the activity of choline oxidase and hence it is preferably used in as small an amount as possible. The amount of 4-aminoantipyrine is greater than $\frac{1}{2}$ μmole and preferably greater than 2 μmoles corresponding to liberated hydrogen peroxide, and the amount of peroxidase is greater than 0.1 unit and preferably greater than 0.2–0.5 unit. 4-aminoantipyrine can be replaced by 4-aminophenazone. The reagents can be prepared previously as a solution. Hydrogen peroxide is also quantitatively determined by a combination of 2,6-dichlorophenol indophenol and peroxidase, guaiacol and peroxidase, or homovanillic acid and peroxidase.

In the above quantitative assay of hydrogen peroxide, betaine and oxygen, and the quantitative determination of hydrogen peroxide, the combination of peroxidase and coloring agent is preferably used due to its accuracy and easiness.

Accordingly, choline or betaine aldehyde in a sample can be quantitatively assayed by the amount of generated hydrogen peroxide, produced betaine or consumed oxygen and the plotting of the standard curve thereof. The purity of choline or betaine aldehyde can be directly assayed and also the derivatives of choline can easily be assayed.

The quantitative determination of choline can also be performed by assaying the amount of intermediate betaine aldehyde or corresponding hydrogen peroxide formation. The intermediate betaine aldehyde is further oxidized by choline oxidase to form hydrogen peroxide and therefore it leads to noticeable error. To avoid the error, the addition of an inhibitor such as the inhibitor which comprises Schiff base with betaine aldehyde or altering the reaction route of betaine aldehyde dehydrogenase and NAD or NADP system may preferably be recommended.

Various compositions of the reagents and enzymes can be provided as a kit for analysis.

In the analytical methods hereinbefore explained, the specific enzyme phospholiphase D which catalyzes a reaction on phospholipid and liberates choline is used. Since this phospholipase D is a very specific and advantageous enzyme for the purpose of the quantitative determination of choline and derivatives thereof in the present invention, a more detailed explanation will be given below.

Advantageously, the phospholipase used in this invention is produced by culturing *Streptomyces hachijoensis* A-1143 or *Streptomyces chromofuscus* A-0848 which strains have been deposited in the Institute for Microbial Industry and Technology, Japan as FERM-P No. 1329 and FERM-P No. 3519, respectively.

The taxonomic properties of the strain *Streptomyces chromofuscus* A-0848 FERM-P No. 3519 and physicochemical properties of phospholiphase D are as follows:

Taxonomic properties:

(a) Morphology:

According to macroscopic observation, the spore-bearing aerial mycelium is gray, and the substrate mycelium is yellowish brown or yellowish orange. No soluble pigment is formed.

Microscopic observations on starch inorganic salts agar medium at 30° C. for 10–15 days culturing are as follows:

Aerial mycelium: diameter 0.6–0.8μ; wavy and simple branching; forms spore chains; 1–3 coiled spirals of spore chains and a few of 4–5 coiled spirals; sometimes flexuous and straight spore chains.

Spore: spherical or elliptical, 0.6–0.8 × 0.7–0.9μ, spiny surface.

Substrate mycelium: developed with flexuous branching; diameter 0.4–0.6μ; no fission and spore bearing.

No flagellous spore and sporangium.

(b) Analysis of whole cell hydrolysis (diaminopimelic acid):

Mycelium grown on Bennett's medium for 6 days with shaking culture was analyzed according to the method of Becker et al. [Appl. Microbiol., 12(5), 421–423 (1964)]. LL-diaminopimelic acid was detected but the meso form was not found.

(c) Cultural characteristics:

Various media indicated below were cultured at 30° C. for 20 days.

Abbr.: G = growth, A = aerial mycelium, S = soluble pigment.

(1) Sucrose nitrate agar:
 G: trace, no color. A: trace. S: none.
(2) Glycerin nitrate agar:
 G: moderate — good, pastel orange (4 ic).
 A: none — trace. S: nude tan (4 gc), trace.
(3) Glucose asparagine agar:
 G: moderate, bamboo (2 fb) — amber (3 pe).
 A: poor — moderate, white (a). S: none.
(4) Glycerine asparagine agar:
 G: moderate, golden brown (3 pg — 3 pi).
 A: moderate, silver gray (3 fe) — natural (3 dc).
 S: none.
(5) Starch inorganic salt agar:
 G: moderate — good, golden brown (3 pi) — clove brown (3 pl). A: moderate — good, silver gray (3 fe) — natural (3 dc). S: none.
(6) Tyrosine agar:
 G: moderate — good, golden brown (3 pg — 3 pi). A: moderate — good, silver gray (3 fe) — natural (3 dc). S: none.
(7) Glycerine starch glutamate agar:
 G: moderate — good, rust tan (5 gc) — maple (4 le).
 A: moderate, oyster white (b) — light gray (c).
 S: none.
(8) Oatmeal agar:
 G: moderate — good, mustard gold (2 ne) - golden brown (3 pg). A: moderate — good, natural (3 dc) — beige brown (3 ig). S: none.
(9) Yeast extract malt extract agar:
 G: moderate — good, amber (3 lc) — yellow maple (3 ng). A: moderate, silvery gray (3 fe) — beige brown (3 ig) — beige (3 gc). S: none.
(10) Nutrient agar:
 G: moderate, amber (3 pe). A: trace - poor, white (a). S: none.
(11) Peptone yeast extract iron agar:
 G: moderate — good, surface no color, reverse side, golden brown (3 pg). A: none. S: golden brown (3 pg — 3 pi).
(12) Triptone yeast extract medium:
 G: good, amber (3 nc — 3pc). A: none. S: none — golden brown (3 pg).
(13) Glucose peptone gelatin medium:
 G: poor, golden brown (3 pg). A: none.
 S: golden brown (3 pi).
(14) Skim milk medium:
 G: good — better, light amber (3 ic) — light tan (3 gc). A: none. S: maple (4 le) —pastel orange (4 ic).

(d) Physiological characteristics: (+ = positive, — = negative)

(1) Melanine-like pigment formation: peptone yeast extract iron agar: +; tryptone yeast extract medium: ±; tyrosine agar: -.
(2) Gelatin liquefaction: glucose peptone gelatin medium: +.
(3) Starch hydrolysis; starch inorganic salt agar medium: +.
(4) Milk: coagulation: -, peptonization: +.
(5) Carbon source utilization: D-glucose, L-arabinose, D-mannitol, L-rhamnose, D-xylose; +; inositol, raffinose: ±; sucrose; -.
(6) Growth temperature: 10–47° C.

The aerial mycelium is developed from substrate mycelium without fission and has many spore chains. Characteristics of diameter of mycelium and shape of spore, or cell wall containing LL-diaminopimeric acid identify the strain as belonging to genus Streptomyces. The characteristics such as grayish aerial mycelium, spiral spore chains, spiny spore surface, yellowish brown to yellowish orange substrate mycelium, no soluble pigment formation, melanin-like pigment formation on peptone yeast extract iron agar medium, no melanin-like pigment formation on tyrosine agar medium and carbon source utilization on various carbon sources, distinguish this strain as *Streptomyces chromofuscus* (Preobrazhenskaya et al.) Pridham et al., and named *Streptomyces chromofuscus* A-0848.

Culturing the strain and producing the phospholipase D are conventionally performed as illustrated in Example 1 hereinbelow.

Physico-chemical properties of this phospholipase D are illustrated as follows:

(1) Enzyme action:

The enzyme catalyzes the hydrolysis of the ester bond of phosphates and the basic nitrogen group of phospholipids and liberates phosphorous compounds and corresponding basic nitrogen compounds.

(2) Assay method:

To a reagent containing 0.2 M tris-HCl buffer (pH 8.0, 0.1 ml), 10 mM lecithin emulsion (0.1 ml), 0.1 M calcium chloride (0.05 ml), 1% Triton X-100 (0.1 ml) and water (0.1 ml) was added enzyme solution (0.05 ml). After 10 minutes incubation at 37° C., the mixture was boiled to stop the enzyme reaction and cooled to 37° C. 4-aminoantipyrine (3 mg/ml, 0.1 ml), peroxidase (2 u/ml, 0.1 ml), 0.1% phenol (0.1 ml), choline oxidase (12 u/ml, 0.1 ml) and water (0.1 ml) were added thereto. After incubation at 37° C. for 20 minutes, 1% Triton X-100 (2 ml) was added and the optical density was measured at 500 nm.

A unit of enzyme activity is defined as the activity of enzyme which liberates 1$\mu$ mole of choline per minute. The activity of enzyme (unit/ml) is given by:

Units/ml = $\Delta A_{500} \times 0.55$ where $\Delta A_{500}$ is the optical density at 500 nm.

(3) Substrate specificity:

Relative activity on several substrates is as follows:

| Substrate | Relative activity |
| --- | --- |
| Lecithin | 51% |
| Sphingomyelin | 19% |
| Lysolecithin | 100% |

Figure 7:
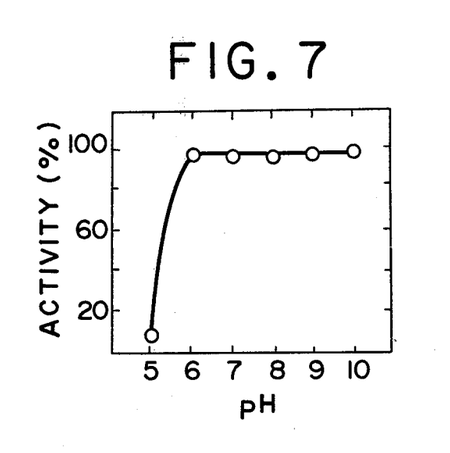
FIG. 7: pH-stability of phospholipase D.

(4) pH Stability:

Enzyme solution (1 mg/ml) was incubated at 37° C. for 60 minutes on various buffer solutions (pH 5: acetate buffer, pH 6–7: dimethylglutarate - NaOH buffer, pH 8–9: tris-HCl buffer, pH 10: glycine-NaOH buffer, each 10 m moles and the phospholipase D activity was assayed. As shown in FIG. 7, the enzyme is stable at pH 7–9.

Figure 8:
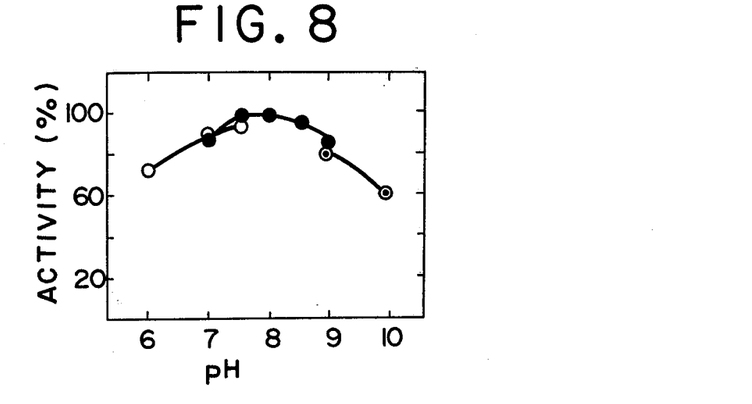
FIG. 8: optimum pH of phospholipase D.

(5) Optimum pH:

As shown in FIG. 8, the optimum pH of the enzyme is pH 5–8.

Figure 9:
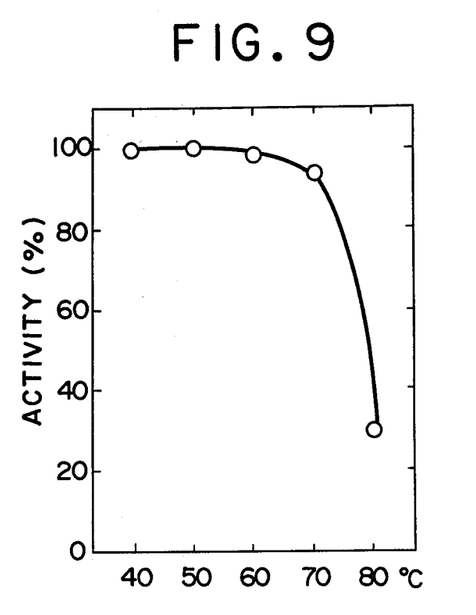
FIG. 9: heat stability of phospholipase D.

(6) Heat stability:

Enzyme solution (1 mg/ml) in 10 mM tris-HCl buffer (pH 8.0) was incubated for 10 minutes at 40, 50, 60, 70 and 80° C., respectively. As shown in FIG. 9, the enzyme is stable up to 70° C.

(7) Enzyme action on serum phospholipids:

| Sample 1: | 0.2 M tris-HCl buffer (pH 8.0) | 0.2 ml |
| --- | --- | --- |
| | commercial serum | 0.5 ml |
| | 0.1 M CaCl$_2$ | 0.1 ml |
| | 60 u/ml phospholipase D | 0.1 ml |
| | distilled water | 0.1 ml |
| Sample 2: | 0.2 M tris-HCl buffer (pH 8.0) | 0.2 ml |
| | commercial serum | 0.5 ml |
| | 0.1 M CaCl$_2$ | 0.1 ml |
| | 60 u/ml phospholipase D | 0.1 ml |
| | phosphatidate phosphatase* | 2 units |
| | distilled water | 0.1 ml |
| *obtained from | *Streptomyces mirabilis* A-2313 | |
| Sample 3: | 0.2 M tris-HCl buffer (pH 8.0) | 0.2 ml |
| | commercial serum | 0.5 ml |
| | 0.1 M CaCl$_2$ | 0.1 ml |
| | distilled water | 0.2 ml |

Samples 1, 2 and 3 were incubated at 37° C. for 30 minutes, thereafter chloroform-methanol (2:1, 6 ml) and water (1 ml) were added, and mixed well. The mixture was centrifuged for 10 minutes at 3000 r.p.m. The separated chloroform layer was dried in vacuo and chromatographed on a thin layer plate (developer: chloroform:methanol:water = 65:25:3). Phospholipid on the plate was detected by spraying molybdenum blue reagent. Phosphatidylethanolamine, phosphatidylcholine, sphingomyelin, lysophosphatidylcholine and phosphatidic acid were thin layer chromatographed as a control. The results are shown in FIG. 10 wherein: 1: sample 1, 2: sample 2, 3: sample 3, 4: standard phospholipid [phosphatidylethanolamine (A), phosphatidylcholine (B), sphingomyelin (C) and lysophosphatidylcholine (E)] and 5: standard phospholipid [phosphatidic acid (D)].

Figure 10:
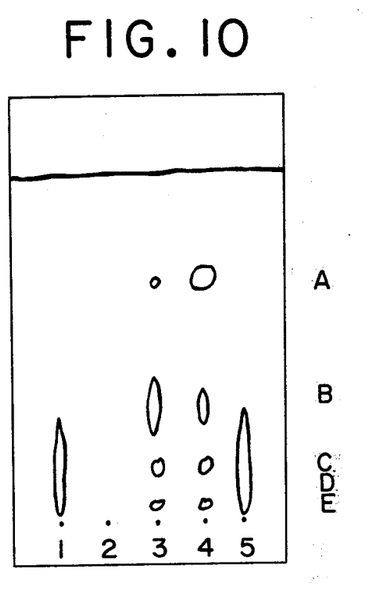
FIG. 10: thin layer chromatogram of phospholipase D action on serum phospholipid.

FIG. 10 shows that serum (sample 3) contains phosphatidylethanolamine, phosphatidylcholine, sphingomyelin and lysophosphatidylcholine. The serum treated with phospholipase D (sample 1) reveals only phosphatidic acid (number 1). Further the serum treated with phospholipase D and phosphatidate phosphatase (sample 2) reveals no spot (number 2). Therefore serum phospholipid is hydrolyzed to phosphatidic acid by phospholipase D and the thus-formed phosphatidic acid is hydrolyzed to inorganic phosphate and diglyceride by phosphatidate phosphatase. The result also shows that serum phosphatidylethanolamine can be a substrate of this phospholipase D.

The phospholipase D obtained from *Streptomyces chromofuscus* A-0848 is superior as to optimum pH, pH stability and heat stability as compared with those of *Streptomyces hachijoensis* A-1143. Further phospholipase D produced by *St. hachijoensis* A-1143 is contaminated with phospholipase C, and thereby is disadvantageous due to side reactions. Therefore phospholipase D produced by *St. chromofuscus* A-0858 is preferably used in the quantitative determination of phospholipid of the present invention.

The following are various embodiments of the manufacturing process of choline oxidase and analytical methods using choline oxidase of the present invention. However, it will be understood that the specification and examples are illustrative but not limitative of the present invention.

EXAMPLE 1

A medium (100 ml) comprising choline (1.0%), KCl (0.5%), K$_2$HOP$_4$ (0.1%), MgSO$_4$.7H$_2$O (0.05%), yeast extract (0.25%), fish soluble (1.0%) and disform CA-200 (0.1%) in a 500 ml Erlenmeyer flask was sterilized at 120° C. for 20 minutes. *Arthrobacter globiformis* B-0577 FERM-P No. 3518 inoculated therein was cultured at 30° C. for 1 day as a seed culture, which was transferred to the same sterilized medium (10 l) in a 30 liter jar fermenter and cultured at 30° C. for 2 days, at 200 r.p.m., aeration 20 l/min. Bacterial cells centrifugally collected were washed with a solution (1 lit.) consisting of 10 mM tris-HCl buffer (pH 8.0), 2 mM EDTA and 1% KCl, lysozyme chloride (200 mg) was added and stirred at 37° C. for 30 minutes. To the supernatant obtained centrifugally at 5000 r.p.m. for 15 minutes was added acetone (1 lit.) and the impure precipitate was separated. Further acetone was added up to 65% concentration, then the precipitate, which was collected centrifugally at 5000 r.p.m. for 15 minutes, was dissolved in a solution (40 ml) consisting of 10 mM tris-HCl buffer (pH 8.0), 2 mM EDTA and 1% KCl. To the supernatant was added saturated ammonium sulfate (60 ml) and stirred for 15 minutes, then centrifuged at 12000 r.p.m. for 15 minutes. The precipitate was dissolved in a mixed solution (15 ml) of 10 mM phosphate buffer (pH 7.0) and 2 mM EDTA and desalted through a Sephadex G-25 column (flow rate: 30 ml/hour). The desalted solution was subjected to a DEAE-cellulose column (2.0 × 7.0 cm, buffered with pH 7.0) to adsorb the enzyme and eluted by the gradient of 0.2 M–0.5 M KCl solutions (flow rate: 1.4 ml/min., each 6 ml fraction). The active fraction (172 ml) was collected and dialyzed for 7 hours (outer solution: mixture of 5 mM phosphate buffer and 2 mM EDTA), then freeze dried. The thus-obtained lyophilizate was dissolved in the mixture of 10 mM tris-HCl buffer (10 ml, pH 8.0), 2 mM EDTA and 1% KCl, and chromatographed on a Sephadex G-200 column (2.8 × 9.5 cm, flow rate: 0.18 ml/min., each 6 ml fraction). Action fractions Nos. 42–48 were collected, freeze dried and the Sephadex column chromatography was repeated. The thus-obtained freeze dried enzyme shows a single protein band on electrophoresis.

Purification data are shown as follows:

| Purification Step | Total Units (u) | Total Protein (mg) | Total Activity (u/mg) |
|---|---|---|---|
| Crude extract | 998 | 7680 | 0.13 |
| Acetone precipitate | 900 | 580 | 1.55 |
| Ammonium sulfate precipitate | 825 | 300 | 2.75 |
| DEAE-cellulose | 420 | 115 | 3.65 |
| First Sephadex G-200 | 390 | 58.2 | 6.70 |
| Second Sephadex G-200 | 380 | 55.9 | 6.80 |

EXAMPLE 2

Quantitative Determination of Choline

Reaction mixture (0.5 ml) consisting of hydrogen peroxide (0.01–0.05 mole), tris-HCl buffer (pH 8.0, 10 μmole), 4-aminoantipyrine (150 μg), phenol (200 μg), peroxidase (0.2μ) and choline oxidase (0.25μ) was incubated at 37° C. for 25 minutes, ethanol (25 ml) was added thereto and the absorbency at 480 nm was measured to obtain the standard curve for hydrogen peroxide.

In the above reaction mixture, hydrogen peroxide was replaced by choline chloride and the absorbency was measured according to the same procedure to determine the choline content quantitatively from the standard curve of hydrogen peroxide.

EXAMPLE 3

In Example 2 choline was replaced by betaine aldehyde and the purity of betaine aldehyde reagent was measured.

EXAMPLE 4

Quantitative Determination of Phospholipid

Reaction mixture:

| 0.2 M tris-HCl buffer (pH 8.0) | 0.15 ml |
|---|---|
| 3 mg/ml 4-aminoantipyrine | 0.50 ml |

-continued

| 0.1% phenol | 0.30 ml |
|---|---|
| 1% Triton X-100 | 0.30 ml |
| 10 mM CaCl$_2$ | 0.30 ml |
| 15 u/ml choline oxidase | 0.10 ml |
| 2 u/ml peroxidase | 0.10 ml |
| 12 u/ml phospholipase D | 0.10 ml |
| distilled water | 1.15 ml |
| Total | 3.00 ml |

Figure 11:
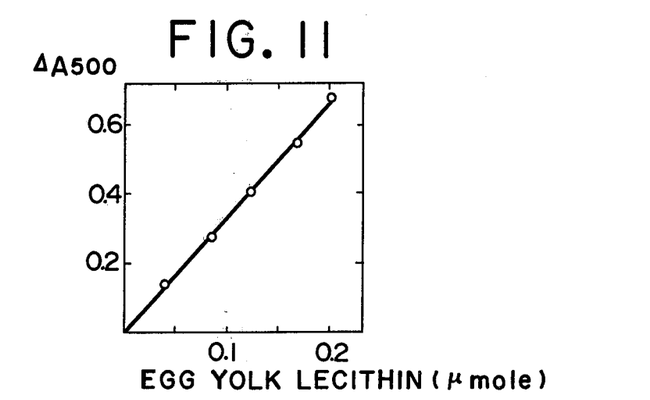
FIG. 11: result of quantitative analysis of egg yolk lecithin.
Figure 12:
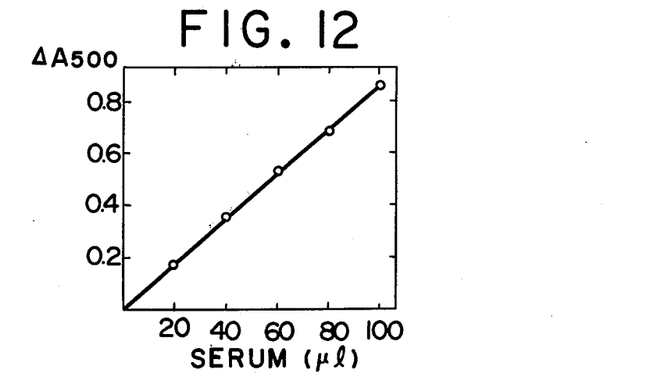
FIG. 12: result of quantitative analysis of serum phospholipid.

Egg Yolk lecithin purified by silica gel column chromatography or commercial serum was incubated with the reaction mixture at 37° C. for 20 minutes and measured by colorimetry at 500 nm to obtain the result as shown in FIG. 11 and FIG. 12, respectively. (FIG. 11: egg yolk lecithin, FIG. 12: commercial serum.) From the result on lecithin in FIG. 11, liberated choline from egg yolk lecithin was determined by the standard cuve of hydrogen peroxide hereinabove exemplified and molar amount of egg yolk lecithin can be determined by the amount of choline. By the same procedure serum phospholipid can be quantitatively determined. The phospholipase D used hereinabove is produced by St. chromofuscus A-0848 and the amount to be used is greater than 0.5 unit, preferably 1–5 units.

EXAMPLE 5

Quantitative Determination of Choline Esterase

Reaction mixture:

| 0.2 M tris-HCl buffer (pH 8.0) | 0.05 ml |
|---|---|
| 3 mg/ml 4-aminoantipyrine | 0.05 ml |
| 0.1% phenol | 0.10 ml |
| 2 u/ml peroxidase | 0.10 ml |
| 20 u/ml choline oxidase | 0.20 ml |
| 50 mM benzoylcholine | 0.02 ml |
| Total | 0.52 ml |

Figure 13:
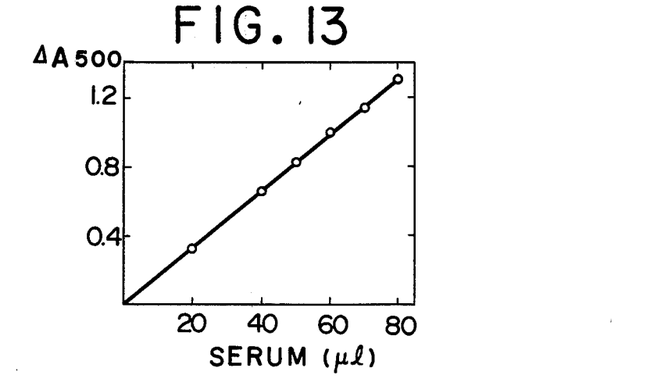
FIG. 13: result of quantitative analysis of human serum choline esterase.

To the reaction mixture was added 10 fold-dilution (physiological saline) human healthy serum and the mixture was incubated at 37° C. for 30 minutes. After adding 0.2 mM neostigmine solution (inhibitor of choline esterase) (3.0 ml), the mixture was allowed to stand for 10 minutes at ambient temperature and colorimetrically measured at 500 nm. The result is shown in FIG. 13.

Serum choline esterase activity can be determined by measuring the amount of generated choline from benzoylcholine in a reaction mixture. The liberated choline is determined by the system of choline oxidase, peroxidase, 4-aminoantipyrine and phenol.

One unit of choline esterase activity is defined as the amount which generates 2 μ moles of hydrogen peroxide per minute at 37° C.

Activity (u/ml) = $\Delta A_{500}$/min × 4.8

The combination of choline esterase and benzoylcholine hereinabove exemplified can be replaced by the other combination of hydrolase of choline derivatives and choline derivatives, and thus can be provided the quantitative analytical systems for various enzyme activities and choline derivatives.

EXAMPLE 6

Production pf Phospholipase D.

A medium consisting of peptone 2%, lactose 2%, NaCl 0.1%, KH$_2$PO$_4$ 0.05%, MgSO$_4$.7H$_2$O 0.5% and disform BC-51Y 0.5% in a 500 ml Erlenmeyer flask

(sterilized at 120° C., for 20 minutes) was inoculated with *Streptomyces chromofuscus* A-0848 FERM-P No. 3519 and cultured at 26° C. for 3 days. This seed culture was transferred to the same medium (20 l) in a 30 liter jar fermenter and aerobically cultured at 26° C. for 2 days (300 r.p.m. 20 l/min.) The cultured filtrate showed an activity of 0.5 u/ml. Cultured filtrate (18 l) was concentrated up to 3 lit. and acetone (2.4 l) was added thereto. The precipitate was centrifuged off. Acetone (2 lit.) was added to the supernatant and precipitated material was collected and thereafter dissolved in distilled water (500 ml). To the solution was added acetone (350 ml) and the precipitated impurity was separated. Acetone (330 ml) was added to the supernatant, and the precipitate was collected and dissolved in distilled water (200 ml). To the solution was again added saturated ammonium sulfate (200 ml). After collecting by centrifugation, the precipitate was dissolved in distilled water, desalted through Sephadex G-25 and lyophilized to obtain crude powder of phospholipase D (5 u/mg, 700 mg).

From a consideration of the foregoing disclosure, therefore, it will be evident that all of the initially recited objects of the present invention have been achieved.

Although the present invention has been described and illustrated in connection with preferred embodiments, it is to be understood that modifications and variations may be resorted to without departing from the spirit of the invention, as those skilled in this art will readily understand. Such modifications and variations are considered to be within the purview and scope of the present invention as defined by the appended claims.

We claim:

1. An enzyme choline oxidase which has the following properties:
   (1) substrate specificity: a specific activity for a compound of the formula wherein $R_1$ is —CH$_2$OH or —CHO;
   (2) optimum pH: pH 8 (tris-HCl buffer);
   (3) isoelectric point: 4.6 (electrophoresis using carrier-type ampholyte);
   (4) molecular weight: 84,000 ± 2,100 [gel filtration using Sephadex G-150];
   (5) enzyme action: catalyzes the reaction [I] and/or [II]:

2. Choline oxidase as claimed in claim 1 wherein the optimum temperature is about 40° C. (tris-HCl buffer), stable pH is about pH 8 (tris-HCl buffer) and heat stability is below about 40° C. (tris-HCl buffer).

3. A process for production of choline oxidase which comprises culturing a choline oxidase-producing microorganism belonging to genus Arthrobacter in a nutrient culture medium and isolating the choline oxidase thus produced from the cultured mass thereof.

4. A process as claimed in claim 3 wherein the culture medium contains free choline.

5. A process as claimed in claim 3 wherein the choline oxidase-producing microorganism is *Arthrobacter globiformis* B-0577 FERM-P No. 3518.

6. A process as claimed in claim 3 wherein the cultured microorganism belonging to genus Arthrobacter is subjected to lysozyme treatment for the isolation of choline oxidase from the cultured mass.

7. Method for determination of choline or betaine aldehyde, which method comprises treating a sample containing choline or betaine aldehyde with a choline oxidase as claimed in claim 1 and measuring the generated hydrogen peroxide.

8. Method as claimed in claim 7 wherein the said sample comprises a liquid containing choline or betaine aldehyde, or a liquid containing choline derivative or betaine aldehyde derivative and hydrolyzing reagent therefor.

9. Method as claimed in claim 8 wherein the choline derivative is a phospholipid.

10. Method as claimed in claim 9 wherein the phospholipid is lecithin, lysolecithin or a sphingomyelin.

11. Method as claimed in claim 8 wherein the hydrolyzing reagent is phospholipase D.

12. Method as claimed in claim 11 wherein the said phospholipase D is an enzyme obtained from the culture of *Streptomyces chromofuscus* A-0848.

13. Method as claimed in claim 8 wherein the choline derivative is benzoylcholine.

14. Method as claimed in claim 8 wherein the hydrolyzing reagent is choline esterase.

15. Method as claimed in claim 7 wherein the measurement of hydrogen peroxide is carried out by the system comprising one or more chromogens for color development depending on the concentration of hydrogen peroxide.

16. Method as claimed in claim 15 wherein the measurement of hydrogen peroxide is carried out by using peroxidase.

17. Method as claimed in claim 16 wherein the peroxidase is used in an amount of 0.2 to 0.5 unit.

18. Method as claimed in claim 15 wherein the coloring reagent is used in an amount of two molar excess per mole of hydrogen peroxide formed.

19. Method as claimed in claim 15 wherein the said system consists of 4-aminoantipyrine, phenol and peroxidase.

20. Method as claimed in claim 7 wherein the choline oxidase is used in an amount of 1.5 to 5 units.

21. Method as claimed in claim 7 wherein the said sample contains phospholipid, phospholipase D, choline oxidase, 4-aminoantipyrine, phenol and peroxidase.

* * * * *